United States Patent [19]

Chaykovsky et al.

[11] Patent Number: 5,410,079

[45] Date of Patent: Apr. 25, 1995

[54] 5-UREIDO-1,3-DIAMINO-2,4,5-TRINITROBENZENE

[75] Inventors: Michael Chaykovsky, Columbia; Horst G. Adolph, Silver Spring, both of Md.

[73] Assignee: The United States of America as represented by the Secretary of the Navy, Washington, D.C.

[21] Appl. No.: 595,806

[22] Filed: Apr. 2, 1984

[51] Int. Cl.⁶ .................. C07C 127/19; C07C 79/10; C06B 25/04

[52] U.S. Cl. ........................ 564/50; 564/48; 149/105; 149/92

[58] Field of Search .............. 564/48, 50; 149/105

[56] References Cited

U.S. PATENT DOCUMENTS

| | | | |
|---|---|---|---|
| 4,173,591 | 11/1979 | Koppes et al. | 568/933 |
| 4,246,196 | 1/1981 | Arndt et al. | 564/50 |
| 4,281,187 | 7/1981 | Papenfuhs et al. | 564/50 |
| 4,445,948 | 5/1984 | Stanton et al. | 149/105 |

OTHER PUBLICATIONS

Hutchinson et al., "Aminotetryls; synthesis, spectral characterization, thermal decomposition & explosive properties", *Chemical Abstracts*, vol. 102 (2), No. 9048d, 1985.

Koppess et al. "Reaction of 1,3,5-Trifluorotrinitrobenzene with Nucleophiles", J. Chem. Soc., Perkin Trans I, 1981 (7), pp. 1815–1820.

*Primary Examiner*—Gary Geist
*Attorney, Agent, or Firm*—Roger D. Johnson

[57] ABSTRACT

5-ureido-1,3-diamino-2,4-6-trinitrobenzene,

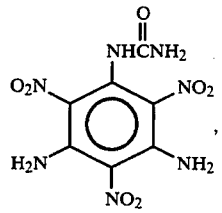

which is prepared by reacting 5-fluoro-1,3-diamino-2,4,6-trinitrobenzene with urea.

1 Claim, 1 Drawing Sheet

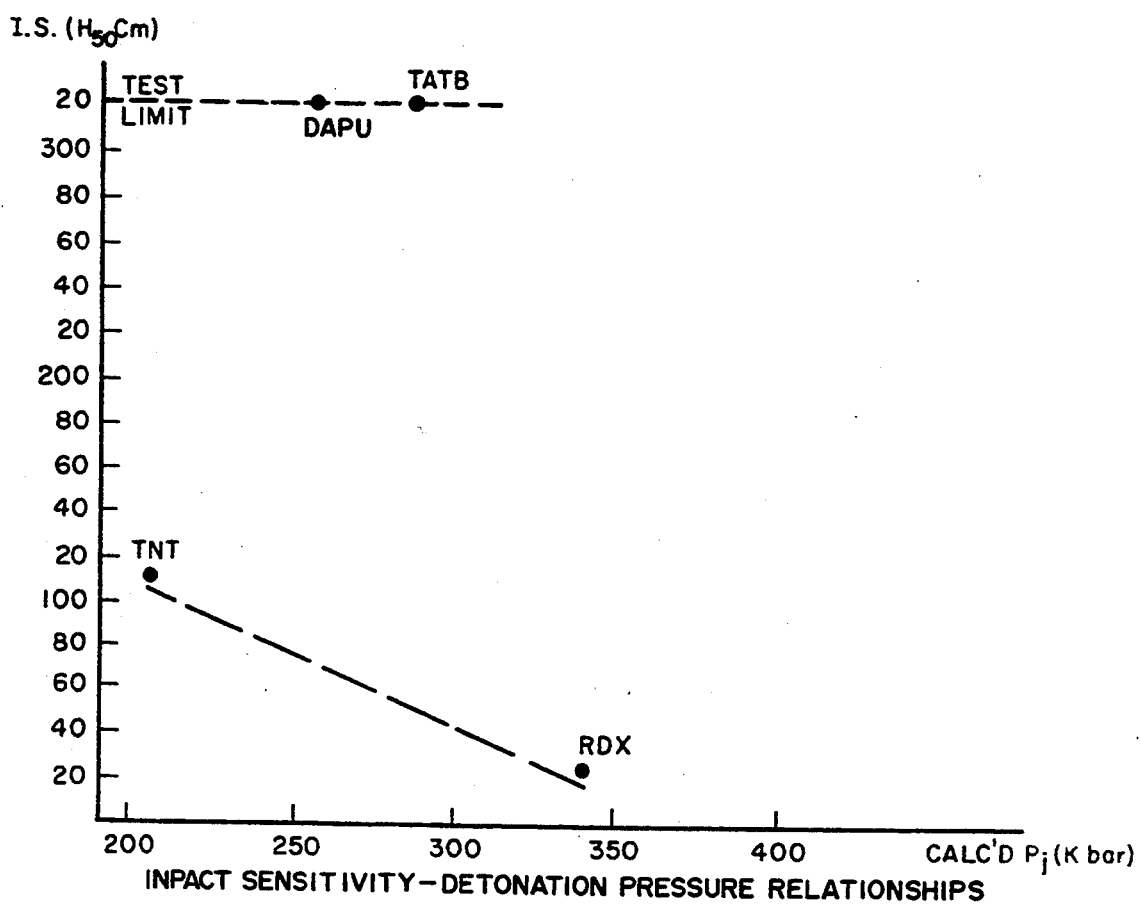

5-UREIDO-1,3-DIAMINO-2,4,5-TRINITROBENZENE

BACKGROUND OF THE INVENTION

This invention genrally relates to aromatic nitro compounds and more particularly to 5-ureido-1,3-diamino-2,4,6-trinitrobenzene and a method of preparation thereof.

Currently used explosive charges contain TNT, RDX, and HMX as the principal ingredients. These compounds are relatively sensitive to impact and other stimuli. Explosive compounds such as 1,3-diamino-2,4,6-trinitrobenzene (DATB) and 1,3,5-triamino-2,4,6-trinitrobenzene (TATB) are less sensitive to impact at comparable performance levels. DATB and TATB are mixed with TNT, RDX, HMX, or mixtures thereof to provide explosives which are less sensitive but which provide comparable detonation pressures.

It would be desirable to provide explosive compositions which are even less sensitive to impact and high temperatures while still providing high detonation pressures.

SUMMARY OF THE INVENTION

Accordingly, it is an object of this invention to provide a new explosive compound and a method of preparing it.

Another object of this invention is to provide a new explosive having a high energy density.

A further object of this invention is to provide a safer explosive which is less likely to detonate accidently.

These and other objects of this invention are accomplished by providing 5-ureido-1,3-diamino-2,4,6-trinitrobenzene and a method of preparation. The compound is prepared by reaction 5-fluoro-1,3-diamino-2,4,6-trinitrobenzene with urea.

BRIEF DESCRIPTION OF THE DRAWING

A more complete understanding of the invention and the many attendant advantages thereto will be readily appreciated as the same becomes better understood by reference to the following detailed description when considered in connection with the accompanying drawing wherein the impact sensitivity-detonation pressure relationships for 5-ureido-1,3-diamino-2,4,6-trinitrobenzene (DAPU) and three known explosives (TNT, TATB, and RDX) are plotted.

DETAILED DESCRIPTION OF THE INVENTION

Referring to the Figure, 5-ureido-1,3-diamino-2,4,6-trinitrobenzene (DAPU),

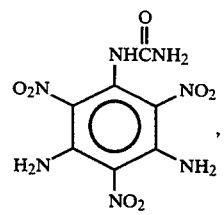

combines a detonation pressure greater than TNT with a high degree of impact insensitivity. Moreover, DAPU offers several advantages over other impact insensitive explosives such as 1,3-diamino-2,4,6-trinitrobenzene (DATB) and 1,3,5-triamino-2,4,6-trinitrobenzene (TATB). First, DAPU is even less impact sensitive than DATB or TATB because of its lower oxygen balance. Second, the DAPU molecular structure provides an additional energy sink via the endothermic conversion of the ureido into an amino group with loss of HCNO at elevated temperature,

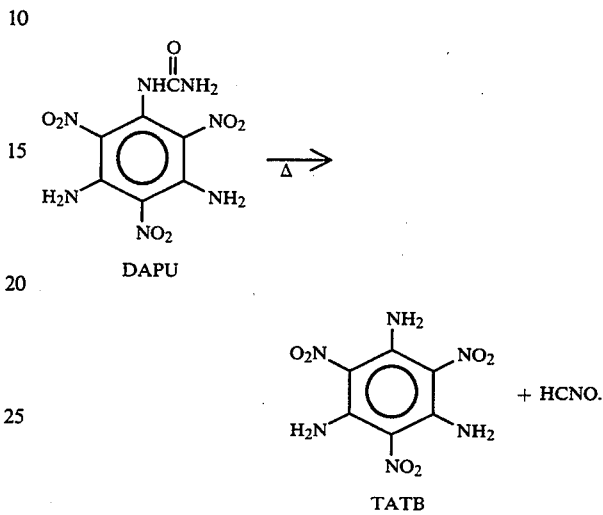

(this conversion is seen in the mass spectrum of DAPU.) Thus, DAPU should be a more effective desensitizing agent than TATB or DATB and provide explosive composites with greater thermal stabilities.

In a typical application, DAPU is combined with another explosive filler such as HMX or RDX in the desired ratio and processed into a PBX or Octol type composition under the same conditions used for RDX or HMX alone.

The compound of this invention, 5-ureido-1,3-diamino-2,4,6-trinitrobenzene (DAPU), is produced by reacting 5-fluoro-1,3-diamino-2,4,6-trinitrobenzene (F-DATB) with urea:

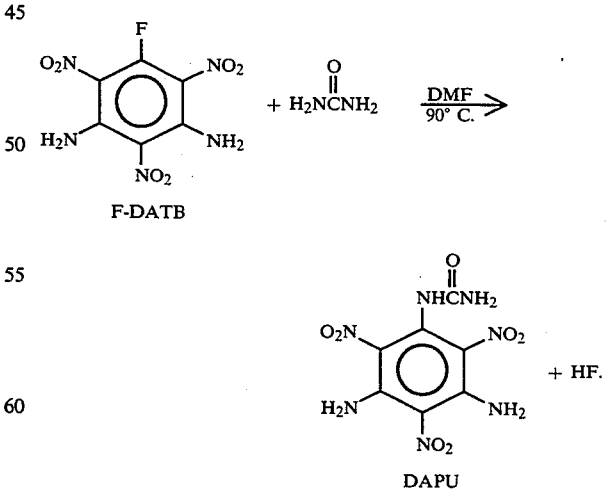

Example 3 illustrates the reaction conditions which are used. N,N'-dimethylformamide (DMF) is the preferred solvent for the reaction step and the subsequent purification steps.

Examples 1 and 2 illustrate a procedure for synthesizing the F-DATB starting material from 1,3,5-trifluorobenzene.

The general nature of the invention having been set forth, the following examples are presented as specific illustrations thereof. It will be understood that the invention is not limited to these specific examples, but is susceptible to various modifications that will be recognized by one of ordinary skill in the art.

Example 1 is incorporated from U.S. Pat. No. 4,173,591, entitled "Process for the Preparation of 1,3,5-trifluoro-2,4,6-trinitrobenzene," which issued on Nov. 6, 1979, to William M. Koppes, Horst G. Adolph, and Michael E. Sitzmann. This example illustrates a method of preparing the 1,3,5-trifluoro-2,4,6-trinitrobenzene starting material.

EXAMPLE 1

1,3,5-trifluoro-2,4,6-trinitrobenzene (Prior Art)

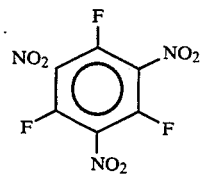

A 3 liter 3-necked Morton flask equipped with Teflon TM paddle stirrer and thermometer and containing 1200 ml of 30% fuming sulfuric acid (8.78 tool $SO_3$) was cooled with an ice-bath while 280 g (2.76 mol) of $KNO_3$ were added in portions to maintain a temperature not exceeding 50° C. The reaction flask was placed in an oil bath and 1,3,5-trifluorobenzene (56.0 g, 0.424 tool) was added through an addition funnel. The addition rate was controlled to maintain the temperature at about 50° C. The funnel was exchanged for a condenser protected with a drying tube (Drierite) and the mixture was heated at 153°–156° C. for 72 hours. The mixture was allowed to cool to 30° C. and extracted in the reaction flask with $CH_2Cl_2$(3×1200 ml). The combined extracts were concentrated by distillation to 250 ml and this solution treated with $Na_2SO_4$ and filtered. Dry hexane (150 ml) was added to the hot filtrate. After treatment with charcoal the hot solution was filtered. A total of 60.8 g of 1,3,5-trifluoro-2,4,6-trinitrobenzene mp 80°–82° C. (54%) was obtained by concentration of the solution and further addition of hexane. Evaporation of the mother liquor left a 1.4 g residue composed of a 26/74 mixture of 1,3,5-trifluoro-2,4,6-trinitrobenzene and 1,3,5-trifluoro-2,4-dinitrobenzene as determined by gas-liquid phase chromatography.

Example 2 illustrates a method of preparing the 5-fluoro-1,3-diamino-2,4,6-tetranitrobenzene (F-DATB) starting material from 1,3,5-trifluoro-2,4,6-trinitrobenzene.

EXAMPLE 2

5-fluoro-1,3-diamino-2,4,6-trinitrobenzene (Prior Art)

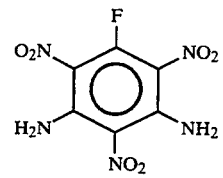

2-amino-2-methylpropane (5.5 g, 75 mmol), in dry dichloromethane (1 500 ml) was added dropwise at 5 ml min$^{-1}$ to a well stirred mixture of 1,3,5-trifluoro-2,4,6-trinitrobenzene (10.0 g, 37.4 mmol), potassium hydrogencarbonate (15.0 g, 15.0 mmol), and dry dichloromethane (400 ml) at −30° C. under nitrogen. Stirring for 15 hours at room temperature, filtration, and evaporation of the solvent gave a product (14.2 g) which had three components by t.l.c. (benzene solvent). This mixture was stirred for 20 hours in trifluoroacetic acid (50 ml) and dichloromethane (10 ml), and the yellow solid filtered off and extracted with boiling 1,2-dichloroethane (1 600 ml). Filtration gave insoluble 1,3,5-triamino-4,5,6-trinitrobenzene (1.15 g). Concentration of the filtrate to 150 ml gave the desired 5-fluoro-1,3-diamino-2,4,6-trinitrobenzene (6.93 g, 70%), m.p. 219°–221° C.

Example 3 illustrates the preparation of the novel compound of this invention.

EXAMPLE 3

5-ureido-1,3-diamino-2,4,6-trinitrobenzene

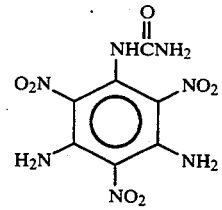

A solution of 5-fluoro-1,3-diamino-2,4,6trinitrobenzene (1.57 g, 6 mmol) and urea (1.80 g, 30 mmol) in 30 ml of dry dimethylformamide (DMF) was heated for 1 hour at 90° C. A yellow precipitate formed after about 5 minutes. The mixture was cooled, poured into 150 ml of cold $H_2O$ and the solid filtered. Trituration of the solid with warm DMF-$H_2O$ (1:1, 100 ml), filtration and drying gave 5-ureido-1,3-diamino-2,4,6-trinitrobenzene (1.67 g, 92.3%): mp 350° C. dec; IR (KBr) 1730 cm$^{-1}$ (C=O); mass spectrum (CI, $CH_4$) m/z 259 (M+1-HNCO, 100).

Anal. Calcd for $C_7H_7N_7O_7$: C, 27.91; H, 2.34; N, 32.56 Found: C, 27.65; H, 2.32; N, 32.31.

Obviously, numerous modifications and variations of the present invention are possible in light of the above teachings. It is therefore to be understood that within the scope of the appended claim the invention may be practiced otherwise than as specifically described herein.

What is claimed as new and desired to be secured by Letters Patent of the United States is:

1. 5-ureido-1,3-amino-2,4,6-trinitrobenzene,

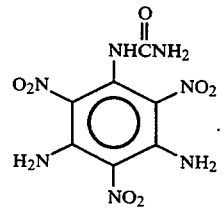

* * * * *